United States Patent
Devinat et al.

(10) Patent No.: US 8,313,472 B2
(45) Date of Patent: Nov. 20, 2012

(54) EMERGENCY EYEWASH STATION AND DISPENSING STRUCTURE THEREFOR

(75) Inventors: Benoit Devinat, Providence, RI (US); Michael C Pereira, Smithfield, RI (US); Breck Petrillo, Warwick, RI (US)

(73) Assignee: Sperian Eye & Face Protection, Inc. a Delaware corporation, Smithfield, RI (US)

( * ) Notice: Subject to any disclaimer, the term of this patent is extended or adjusted under 35 U.S.C. 154(b) by 760 days.

(21) Appl. No.: 11/685,876

(22) Filed: Mar. 14, 2007

(65) Prior Publication Data

US 2007/0219511 A1    Sep. 20, 2007

Related U.S. Application Data

(60) Provisional application No. 60/743,484, filed on Mar. 15, 2006.

(51) Int. Cl.
| | |
|---|---|
| *A61M 35/00* | (2006.01) |
| *A61H 33/04* | (2006.01) |
| *B65D 35/00* | (2006.01) |
| *B65D 37/00* | (2006.01) |
| *B65D 35/28* | (2006.01) |
| *B65D 35/54* | (2006.01) |
| *B65D 35/56* | (2006.01) |
| *B67D 7/06* | (2010.01) |

(52) U.S. Cl. ........ 604/300; 604/289; 604/290; 604/294; 604/295; 604/297; 604/298; 604/301; 604/302; 222/92; 222/94; 222/95; 222/96; 222/97; 222/103; 222/105; 222/106; 222/184; 222/185.1

(58) Field of Classification Search .................. 604/289, 604/290, 294, 295, 297, 298, 300, 301, 302, 604/413, 414; 4/615, 616, 620, 621, 625, 4/624, 626, 627, 630; 222/92, 94, 95, 96, 222/97, 103, 105, 106, 184, 185.1; D23/201, D23/283; 285/26, 29, 35, 308, 320
See application file for complete search history.

(56) References Cited

U.S. PATENT DOCUMENTS 29,476 A    8/1860    Ender
(Continued)

FOREIGN PATENT DOCUMENTS

CN    1625382    6/2005
(Continued)

OTHER PUBLICATIONS

All Safety Products, Inc. "www.allsafetyproducts.biz", Gravity Fed Eye Wash Station.

(Continued)

*Primary Examiner* — Tatyana Zalukaeva
*Assistant Examiner* — Adam Marcetich
(74) *Attorney, Agent, or Firm* — Barlow, Josephs & Holmes, Ltd.

(57) ABSTRACT

An emergency eyewash station and dispensing structure therefore is disclosed. The emergency eyewash station includes a main body configured and arranged to hold and dispense eyewash fluid therefrom, an actuator arm assembly movable from a closed position to an open position, and a dispensing structure having an eyepiece sealed by a membrane. The eyepiece is in fluid connection with the eyewash fluid contained in the main body. The dispensing structure is removably coupled to the actuator arm assembly such that when the actuator arm assembly is moved from the closed position to the open position, the membrane is unsealed and the eyewash fluid dispenses from the eyepiece.

14 Claims, 12 Drawing Sheets

U.S. PATENT DOCUMENTS

| | | | |
|---|---|---|---|
| 593,191 A * | 11/1897 | Bernhardt | 285/280 |
| 623,416 A * | 4/1899 | McCrory | 285/66 |
| 1,638,159 A | 8/1927 | Hopewell | |
| 2,468,849 A * | 5/1949 | Trainor | 285/314 |
| 2,910,064 A | 10/1959 | Brangaitis | |
| 2,999,248 A | 9/1961 | Logan et al. | |
| 2,999,249 A | 9/1961 | Logan et al. | |
| 3,035,737 A | 5/1962 | Speas | |
| 3,106,722 A | 10/1963 | Logan et al. | |
| 3,339,947 A * | 9/1967 | Maisey | 285/315 |
| 3,871,554 A | 3/1975 | Huck | |
| 3,904,083 A | 9/1975 | Little | |
| 3,934,590 A * | 1/1976 | Campagna et al. | 604/302 |
| 4,012,798 A | 3/1977 | Liautaud | |
| D250,594 S | 12/1978 | Gardner | |
| 4,131,115 A | 12/1978 | Peng | |
| 4,220,360 A * | 9/1980 | Jacek et al. | 285/317 |
| 4,232,671 A | 11/1980 | Crump | |
| 4,259,953 A * | 4/1981 | Shaw | 604/302 |
| 4,363,146 A | 12/1982 | Liautaud | |
| 4,493,119 A | 1/1985 | Baumann | |
| 4,527,716 A | 7/1985 | Haas et al. | |
| 4,641,384 A | 2/1987 | Landsberger et al. | |
| 4,675,924 A | 6/1987 | Allison et al. | |
| 4,688,276 A | 8/1987 | Allison et al. | |
| 4,750,643 A | 6/1988 | Wortrich | |
| 4,758,237 A | 7/1988 | Sacks | |
| 4,769,863 A | 9/1988 | Tegg et al. | |
| 4,784,652 A | 11/1988 | Wilkstrom | |
| 4,881,283 A | 11/1989 | Liautaud | |
| 4,928,697 A | 5/1990 | Hsu | |
| 4,938,421 A | 7/1990 | Berfield et al. | |
| 4,939,800 A * | 7/1990 | Fiorentino et al. | 4/620 |
| 4,998,850 A | 3/1991 | Crowell | |
| 5,008,963 A | 4/1991 | Stein | |
| 5,046,648 A | 9/1991 | Herbstzuber | |
| 5,150,811 A | 9/1992 | Kelston | |
| 5,157,798 A | 10/1992 | Van Kammen | |
| 5,170,518 A | 12/1992 | Warriner | |
| 5,171,306 A | 12/1992 | Vo | |
| 5,195,655 A | 3/1993 | Bukhman | |
| 5,201,726 A | 4/1993 | Kirkham | |
| 5,216,765 A | 6/1993 | Paterson et al. | |
| 5,230,109 A | 7/1993 | Zaccai et al. | |
| D342,309 S | 12/1993 | Paterson et al. | |
| 5,320,615 A | 6/1994 | Van Keuren | |
| 5,334,180 A | 8/1994 | Adolf et al. | |
| 5,381,567 A | 1/1995 | Tanner et al. | |
| 5,401,259 A | 3/1995 | Py | |
| 5,530,972 A | 7/1996 | Tanner | |
| 5,531,707 A | 7/1996 | Kers | |
| 5,566,406 A | 10/1996 | Demeny et al. | |
| 5,607,410 A | 3/1997 | Branch | |
| 5,634,458 A | 6/1997 | Joshi et al. | |
| 5,678,255 A | 10/1997 | Stoudamire, Sr. | |
| 5,687,434 A | 11/1997 | Tagg | |
| 5,695,124 A * | 12/1997 | Demeny et al. | 239/327 |
| 5,732,853 A | 3/1998 | Ganzeboom et al. | |
| 5,740,569 A | 4/1998 | Gurries, II et al. | |
| 5,754,900 A | 5/1998 | Suda | |
| 5,754,990 A | 5/1998 | Gurries, II | |
| 5,791,519 A | 8/1998 | Van Marcke | |
| 5,850,641 A | 12/1998 | Demeny et al. | |
| 5,967,197 A | 10/1999 | Shown | |
| 6,029,293 A | 2/2000 | Paterson et al. | |
| 6,070,279 A | 6/2000 | Lundstedt | |
| 6,098,844 A | 8/2000 | Nicolle | |
| 6,131,766 A | 10/2000 | King et al. | |
| 6,142,344 A | 11/2000 | Kai | |
| 6,161,228 A | 12/2000 | Wietecha | |
| 6,176,847 B1 | 1/2001 | Humphreys, Jr. et al. | |
| 6,186,361 B1 | 2/2001 | Teetsel, III | |
| D438,983 S | 3/2001 | Stein | |
| 6,205,599 B1 | 3/2001 | Anders | |
| 6,270,014 B1 | 8/2001 | Bollas et al. | |
| 6,296,626 B1 | 10/2001 | Stein | |
| 6,385,794 B1 | 5/2002 | Miedzius et al. | |
| 6,398,766 B1 * | 6/2002 | Branch | 604/302 |
| 6,432,078 B1 | 8/2002 | Peyman | |
| 6,458,108 B1 | 10/2002 | Tangri | |
| D466,589 S | 12/2002 | Miedzius | |
| 6,510,965 B1 | 1/2003 | Decottignies et al. | |
| 6,520,431 B2 | 2/2003 | Donovan | |
| 6,540,726 B1 | 4/2003 | Follman et al. | |
| 6,554,164 B1 | 4/2003 | Jones | |
| 6,561,383 B1 | 5/2003 | Reddy et al. | |
| 6,595,920 B2 | 7/2003 | Walton | |
| 6,610,036 B2 | 8/2003 | Branch et al. | |
| 6,726,061 B2 | 4/2004 | Good | |
| 6,758,837 B2 | 7/2004 | Peclat et al. | |
| 6,782,568 B2 | 8/2004 | Novak et al. | |
| 6,913,598 B2 | 7/2005 | Tangri | |
| 6,976,279 B1 * | 12/2005 | Berke et al. | 4/620 |
| D529,185 S * | 9/2006 | Zhou | D24/232 |
| 7,188,846 B2 * | 3/2007 | Deavila | 280/47.35 |
| 7,254,848 B2 * | 8/2007 | Johnson et al. | 4/620 |
| 7,278,177 B1 * | 10/2007 | Duffie | 4/620 |
| 2001/0052681 A1 | 12/2001 | Deavila | |
| 2002/0107492 A1 * | 8/2002 | Brach et al. | 604/296 |
| 2003/0032930 A1 | 2/2003 | Branch | |
| 2003/0208186 A1 | 11/2003 | Moreyra | |
| 2004/0204674 A1 | 10/2004 | Anderson et al. | |
| 2004/0244106 A1 | 12/2004 | Chesters | |
| 2005/0054992 A1 | 3/2005 | Madritsch et al. | |
| 2005/0077318 A1 | 4/2005 | Macler et al. | |
| 2005/0217019 A1 | 10/2005 | Johnson et al. | |
| 2007/0089231 A1 * | 4/2007 | Smith et al. | 4/620 |

FOREIGN PATENT DOCUMENTS

| | | |
|---|---|---|
| EP | 0083782 | 7/1983 |
| EP | 0723769 B1 | 7/2001 |
| FR | 2625098 | 6/1989 |
| GB | 1460064 | 12/1976 |
| GB | 2157569 A | 10/1985 |
| JP | 08289916 | 11/1996 |
| JP | 10151148 | 6/1998 |
| JP | 2001079061 | 3/2001 |
| WO | 8702237 A1 | 4/1987 |
| WO | 8705498 A1 | 9/1987 |
| WO | 9619177 A1 | 6/1996 |
| WO | 03065967 A1 | 8/2003 |

OTHER PUBLICATIONS

PlumberSurplus, "www.plumbersurplus.com", Speakman SE-577-SD Emergency Safety Equipment Eyewash Station.

Ramsey Group, "www.ramsey-group.com/pureflow1000.html", Fend-All Pure Flow 1000 Emergency Eyewash Station (FEN-1000).

First Aid Supplies & Safety Products, "www.firstaidandsafetyonline.com/showproduct-catid-24.asp", Eyewash Station, Bradley Eyewash Stations, Emergency Eyewash Station, Portable Eyewash.

* cited by examiner

EMERGENCY EYEWASH STATION AND DISPENSING STRUCTURE THEREFOR

CROSS-REFERENCE TO RELATED APPLICATION

The present application claims priority to earlier filed U.S. Provisional Patent Application Ser. No. 60/743,484, filed Mar. 15, 2006, the contents of which are incorporated herein by reference.

BACKGROUND OF THE INVENTION

1. Field of the Invention

The present invention relates generally to emergency eyewash stations and more particularly to an emergency eyewash station having a mechanism to remove a plug from a sealed end of a fluid dispensing hose connected to a source of "sterile" eyewash fluid.

2. Background of the Related Art

Government and employers are increasingly aware of the need for protecting the health and safety of workers. For this reason, it is common to find eye wash fountains at industrial work sites, laboratories, and other locations where workers are exposed to gaseous fumes, liquids or solid materials which can irritate or injure eyes upon contact therewith. The Occupational Safety and Health Administration (OSHA) has made eye wash fountains mandatory for particular industrial work stations.

Early installations of eye wash fountains employed sprays of regular tap water fed from regular plant plumbing connections. These devices were adequate for a period of time, but suffered from the drawbacks of using the regular water supply. For example, there could be contaminants and bacteria in regular plumbed water. Furthermore, the pressure of regular running water is inconsistent creating an uneven water flow, or in the event of a major facility accident, the water may not be running at all.

Later devices, such as the eye wash fountains disclosed in U.S. Pat. No. 4,012,798 to Liautaud and U.S. Pat. No. 4,363,146 to Liautaud, were self-contained, gravity-fed, and independent of any plumbing connections. These self-contained eye wash fountains typically included a reservoir (or bottles) of wash fluid spaced above two opposed liquid spray nozzles. Upon activating the fluid flow, the wash fluid from the reservoir is fed solely by gravity to the nozzles to cause a gravity-induced spray of wash fluid from the nozzles. These stations provided improved safety in terms of the quality of the water utilized but suffered from low and/or inconsistent water pressure to properly flush the eyes.

In an effort to encourage more suitable eye wash facilities, the American National Standards Institute (ANSI) promulgated voluntary standards for portable eye wash fountains relating to flushing periods and the rate of flow of wash fluid. These standards dictate that portable eye wash fountains should deliver no less than 0.4 gallons per minute (1.5 liters per minute) of eye wash fluid for a time period of minutes. Responsive to the new ANSI standard, several designs emerged that included means for maintaining a constant eye wash flow rate without any powered pumping mechanisms. For example, U.S. Pat. No. 5,566,406, U.S. Pat. No. 5,695,124 and U.S. Pat. No. 5,850,641 all issued to Demeny et al, disclose an emergency eyewash station having a gravity assist mechanism that acts on a flexible reservoir contained in a disposable paperboard box. The self-contained emergency eye wash station generally comprises a housing, a reservoir, and a platen. The housing includes a shelf that supports a pair of flexible containers arranged in side-by-side relation. The flexible containers are of the type generally referred to as "bag-in-a-box" packaging, having an inner flexible plastic bag containing the eyewash fluid, and an outer cardboard box structure, which supports the flexible bag in a predetermined shape. The housing further supports a delivery platform including a nozzle, which is in fluid communication with the flexible container. The nozzle selectively dispenses the eye wash fluid from the flexible container when activated. The housing further includes a drain that captures the eye wash fluid dispensed from the nozzle and directs the eye wash fluid into the reservoir. The reservoir is slidably mounted to the housing and the platen is connected to the reservoir. As the reservoir fills, the platen presses downward on the flexible container with a downward force proportional to a weight of the eye wash fluid collected in the reservoir. The transfer of the weight of the eye wash fluid collected in the reservoir to the platen maintains a constant flow of eye wash fluid dispensed from the nozzle.

The above-noted gravity assist configuration has been very successful in the marketplace and is still in widespread use today. Because the 6 gallons of fluid is divided into two smaller containers, the flexible reservoirs are relatively small and easily replaced by service personnel. In addition, the bag-in-a-box packaging technology is well established, and the costs for producing, maintaining and replacing the disposable cartridges at established intervals of time has heretofore been relatively inexpensive. The costs for this type of system are such that the manufacturer could cost effectively provide a pre-assembled delivery tube and nozzle assembly with each of the disposable cartridges, making installation and replacement that much easier.

However, new ANSI and OSHA regulations have created new issues that will need to be addressed, and will require improvements to the existing designs to maintain compliance. In particular, upcoming OSHA regulations will soon require the use of "sterile" eye wash fluids. The regulatory and production requirements for "sterile" eyewash fluids are far greater than the previous "non-sterile" standards and will make the production of the existing cartridges cost prohibitive.

Accordingly, there is a need in the industry for an improved cartridge assembly which can be filled with a sterile fluid, maintained in a sterile condition for the required shelf-life of the product, provide for safe shipment, handling and storage of the product, and provide for simple installation and replacement, and finally provide a reliable dispensing arrangement for emergency use. Furthermore, there is a need for an improved delivery system which can accommodate the different requirements of the new "sterile" cartridge assemblies, while reducing costs and maintaining simple installation and upkeep of the system.

SUMMARY OF THE INVENTION

The emergency eyewash station of the present invention addresses the problems of the prior art by uniquely providing an emergency eyewash station including an improved cartridge assembly having a sterile "bag" or bladder with a fluid hose having a sealed eyepiece on a dispensing structure at one end, and an actuation mechanism to tear the seal free from the eyepiece upon actuation of the unit.

In particular, the emergency eyewash station of the present invention has a dispensing unit with a pivoting actuator arm assembly having a pair of spring-biased locking members. The actuator arm assembly is configured to pivot between an upright closed position and an open activated position. The locking members are configured and arranged to securely receive the dispensing structure, and may be configured to be selectively releasable therefrom. The seal on the eyepiece of the dispensing structure is secured to the dispensing unit and is configured to peel or tear away from the eyepiece as the actuator arm assembly is pivoted to the open position from the closed position.

BRIEF DESCRIPTION OF THE DRAWINGS

These and other features, aspects, and advantages of the present invention will become better understood with reference to the following description, appended claims, and accompanying drawings where:

DESCRIPTION OF THE PREFERRED EMBODIMENT

Figure 1:
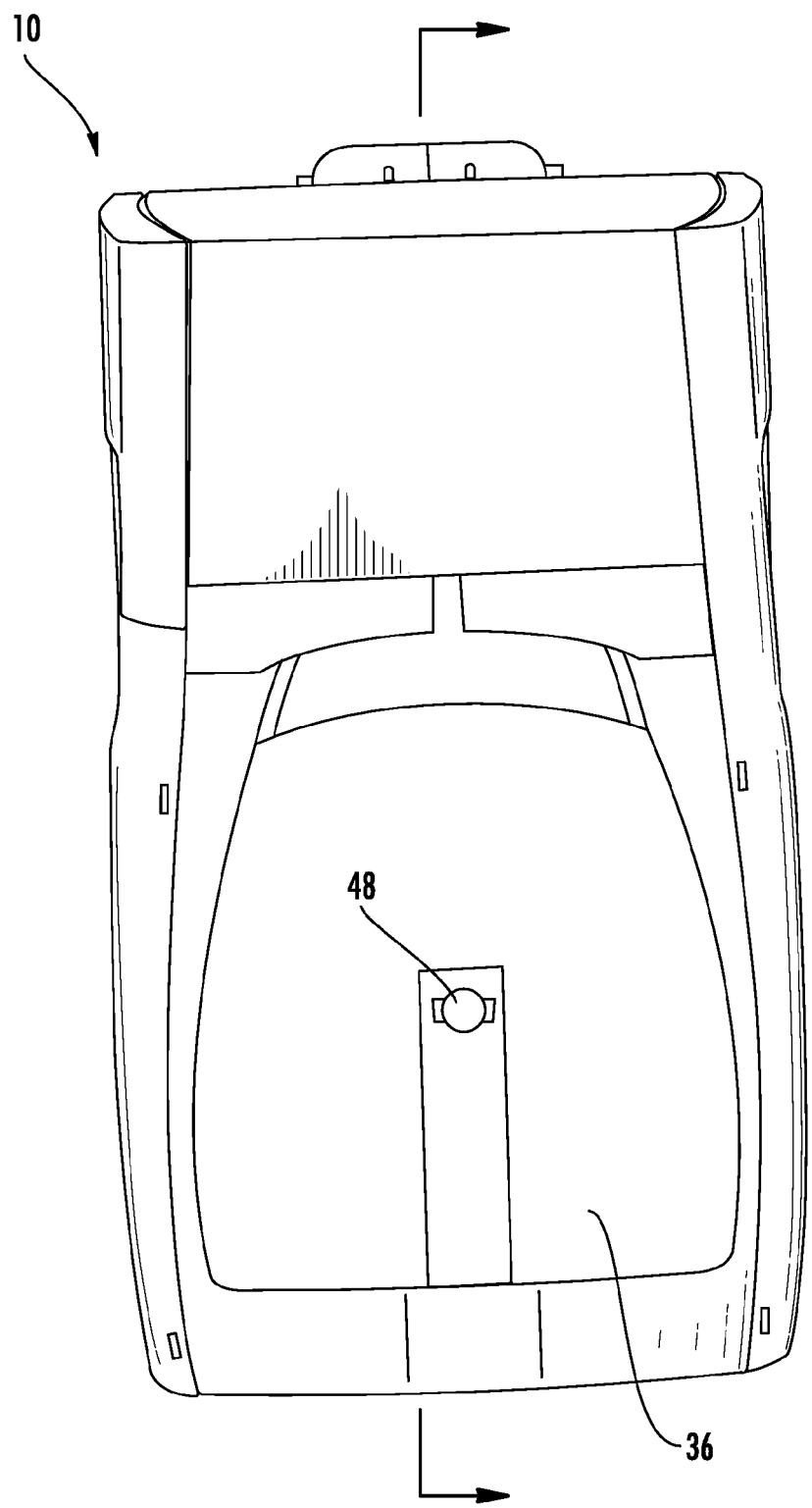
FIG. 1 is a front perspective view of the preferred embodiment of the emergency eyewash station of the present invention.

Referring to FIG. 1, the emergency eyewash station of the present invention is shown generally at 10. As will be described in greater detail below, the emergency eyewash station 10 of the present invention includes an eyewash cartridge assembly 12 and a dispensing structure 22 (best seen in FIG. 2A), which is operable for dispensing eyewash fluid from the cartridge assembly 12 upon activation of a pivoting actuator arm assembly 36.

Figure 2A:
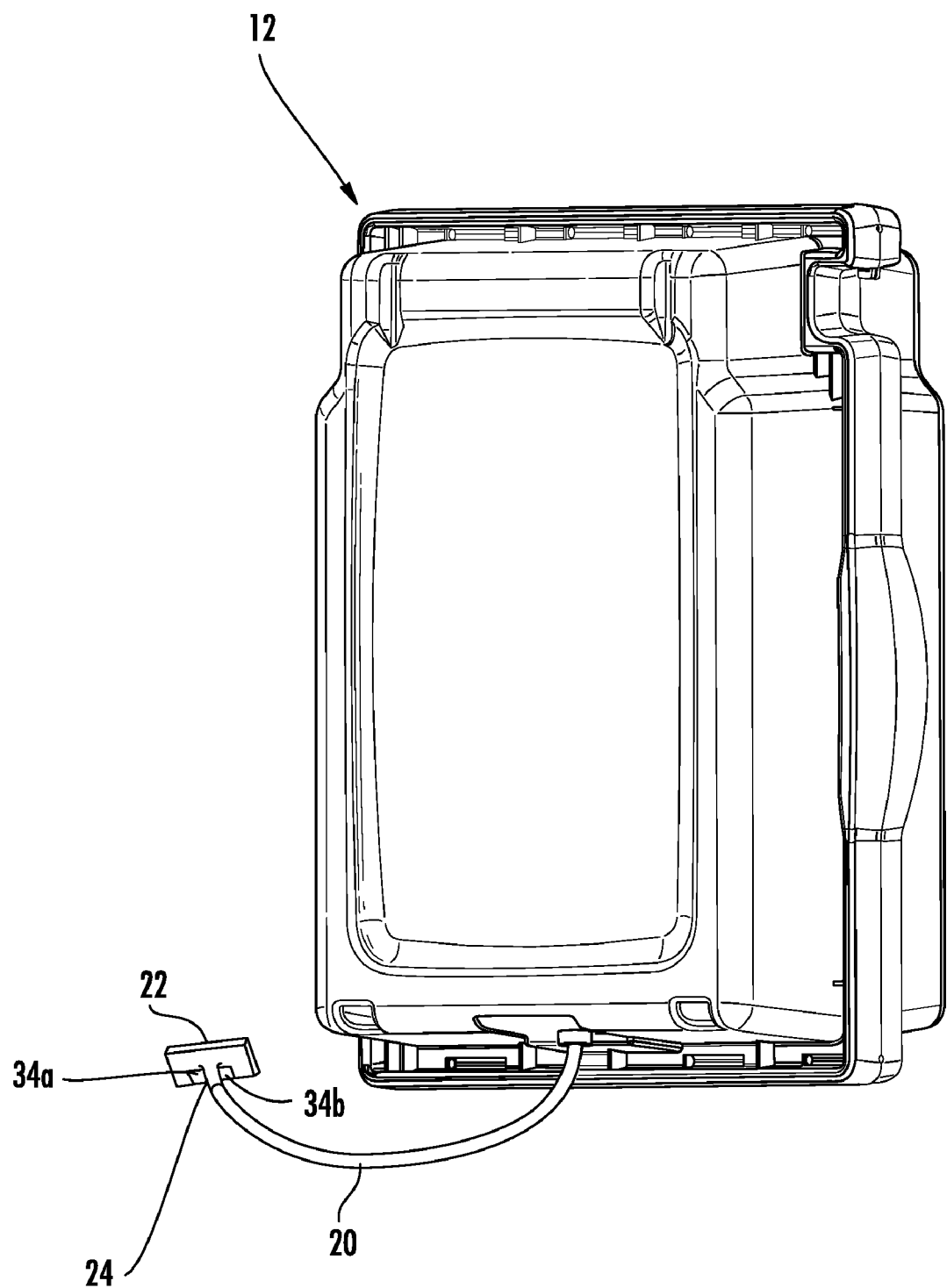
FIG. 2A is front perspective view of the cartridge for the preferred embodiment of the emergency eyewash station of the present invention.
Figure 2B:
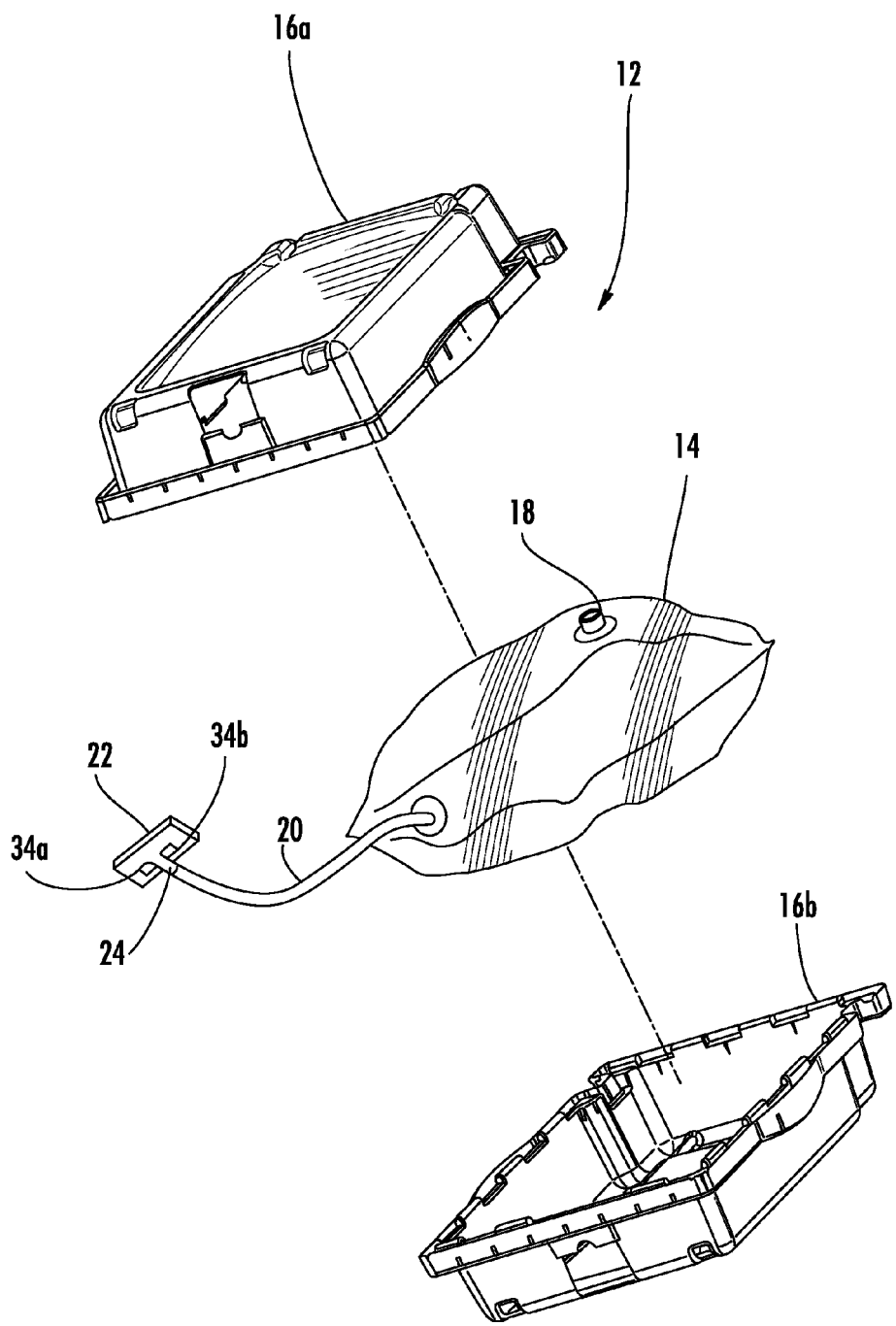
FIG. 2B is an exploded view of the cartridge of the preferred embodiment of the emergency eyewash station of the present invention.

As shown in FIGS. 2A and 2B, the cartridge assembly 12 generally comprises a rigid plastic, outer housing 16 and a disposable flexible inner bladder 14 or bag containing a sterilized eyewash fluid therein.

The housing 16 is formed from two symmetrically identical housing sections 16a, 16b, each having interfitting mating formations that permit the housing sections 16a, 16b to be snap-fit together and maintained in assembled relation.

The flexible bag 14 comprises a flexible plastic material configured for optimal displacement and capacity within the housing 16. The flexible bag 14 is filled using a proprietary filling system through a filling port 18 that maintains sterility of the inside of the bag 14 and the fluid during the filling process. Also connected to the flexible bag 14 is a hose 20 with a dispensing structure 22 at the opposite end.

Figure 3A:
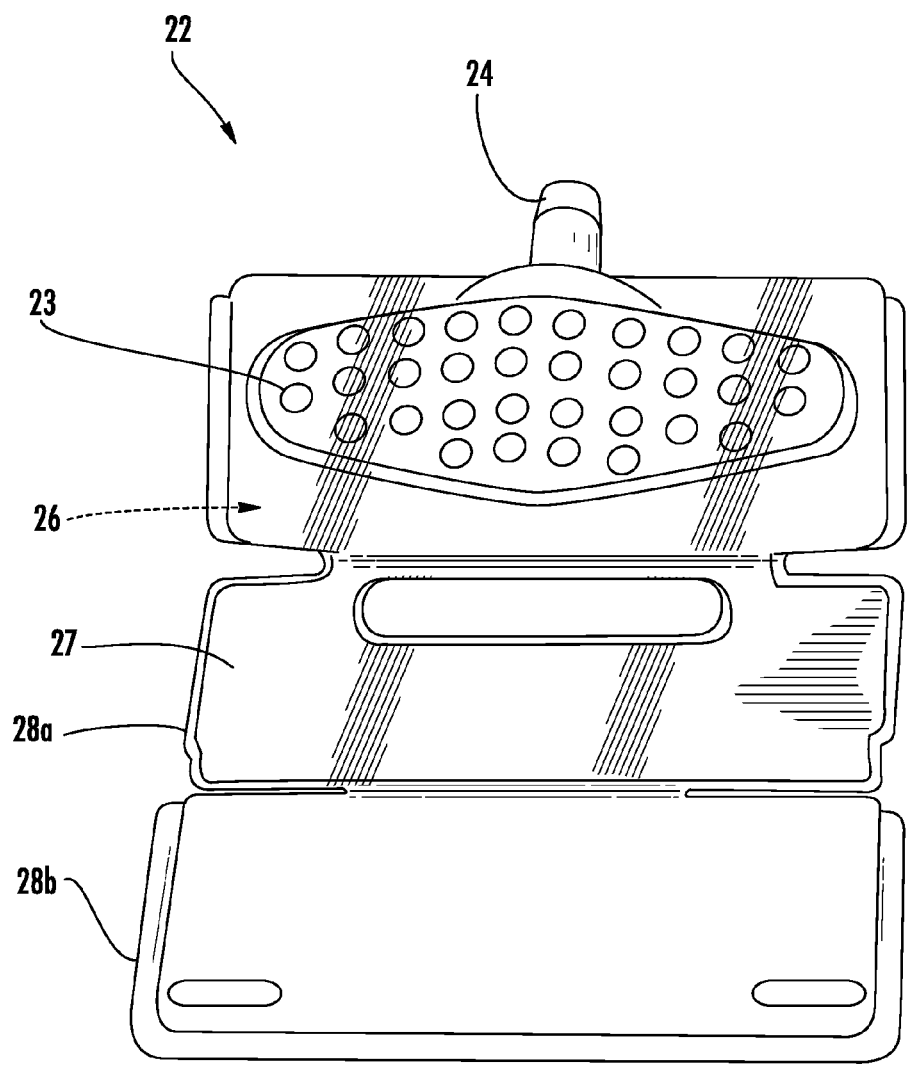
FIG. 3A is a front perspective view of the dispensing structure and clip body unfolded.
Figure 3B:
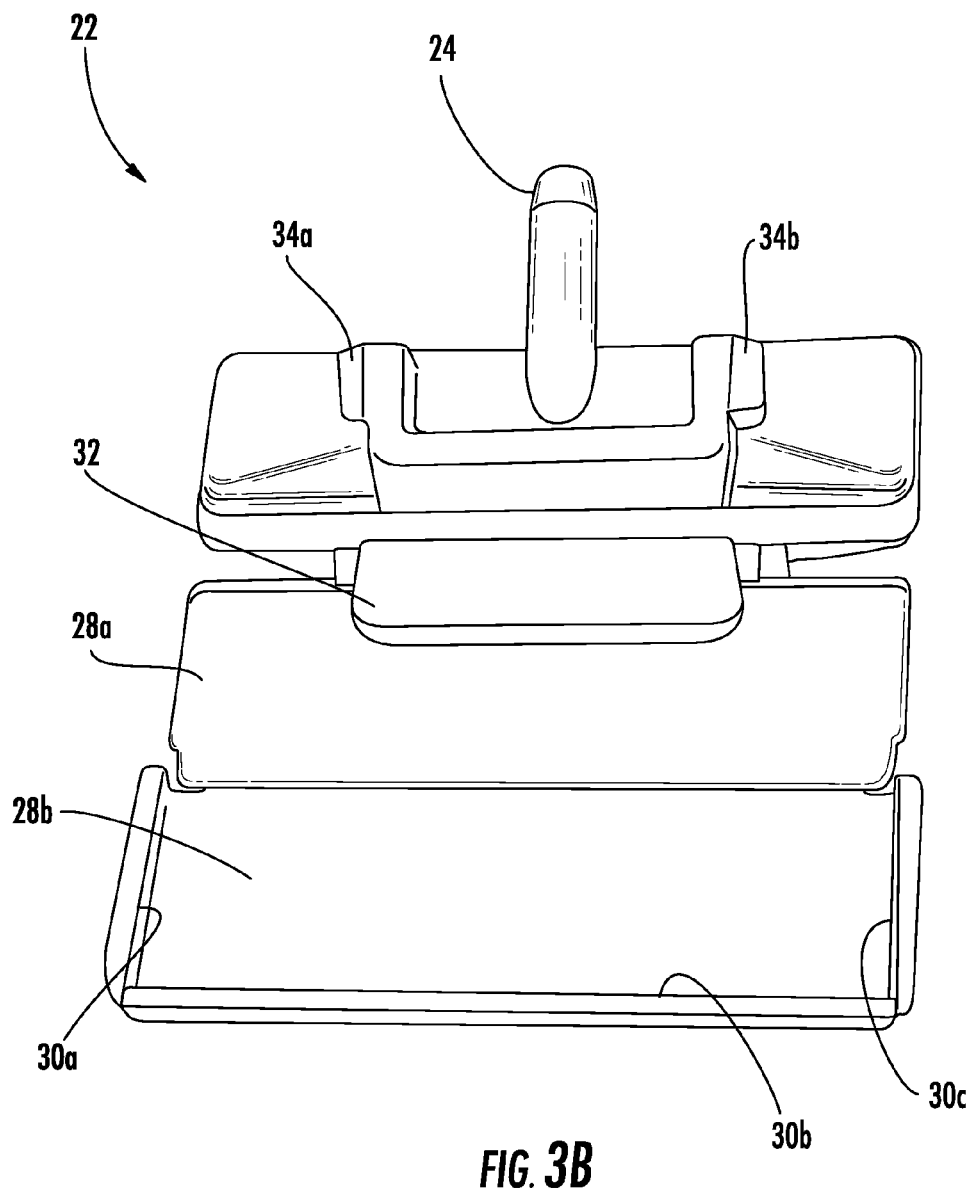
FIG. 3B is a rear perspective view of the dispensing structure and clip body unfolded.
Figure 3C:
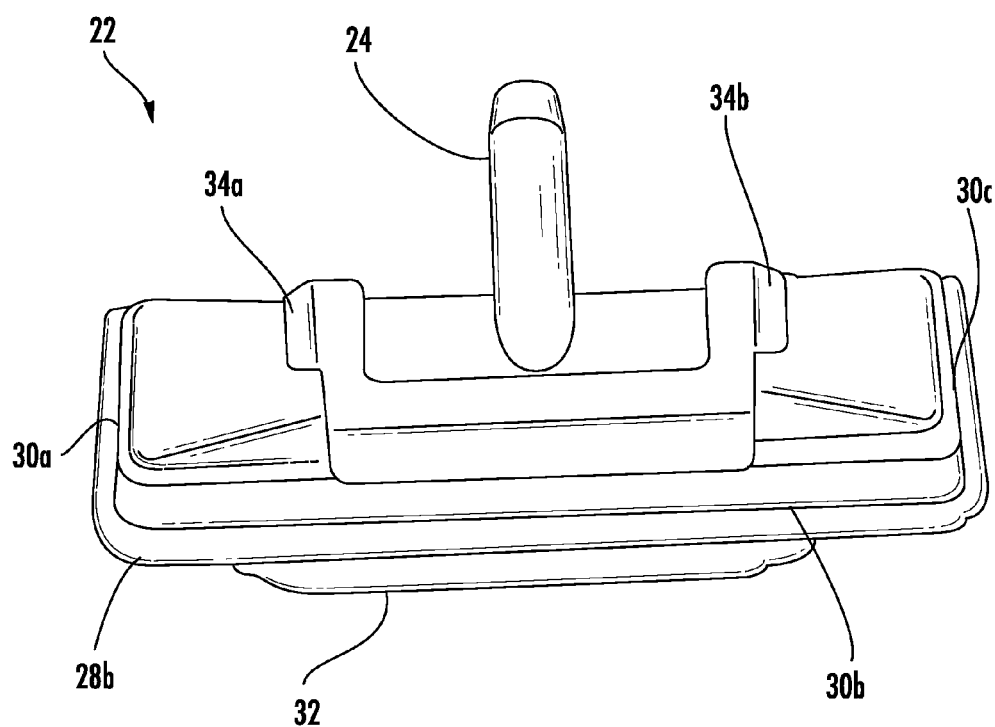
FIG. 3C is a rear perspective view of the dispensing structure and clip body folded and ready for use in the emergency eyewash station of the present invention.

Referring to FIGS. 3A, 3B and 3C, the dispensing structure 22 has an eyepiece 23 extending from a forward facing portion of the dispensing structure 22 and a hose connector 24 extending from a rear facing portion of the dispensing structure 22. The eyepiece 23 is in fluid connection with the hose connector 24, hose and flexible bag 14 as shown in FIGS. 2A and 2B. However, for ease of illustration, FIGS. 3A, 3B, and 3C, illustrate the dispensing structure 22 is shown disconnected from the hose 20 and flexible bag 14.

The eyepiece 23 is sealed closed by a membrane 26 with a tab 27 extending from one end. The tab 27 of the membrane 26 is trapped between two halves of a clip body 28a, 28b that fold closed and snap-fit together to securely hold the tab 27 of the membrane 26 to the clip body 28a, 28b. Once snapped closed, the clip body 28a, 28b is folded over onto the dispensing structure 22.

The retaining structures 30a, 30b, 30c on the outboard edges of the clip body 28b attach to the outer edges of the dispensing structure 22 and hold the clip body 28a, 28b onto the dispensing structure 22, which is shown in FIG. 3C. On the opposite side of the clip body 28a is a cantilevered spring arm 32 for attaching the clip body 28a, 28b to the eyewash station 10, which will be further described below. Extending from a rear facing portion of the dispensing structure 22 is a pair of opposing and outwardly facing hooks 34a, 34b for connecting the dispensing structure 22 to the pivoting actuator arm assembly 36, which will also be more fully described below. Each hook 34a, 34b has a sloped surface thereon.

Figure 4:
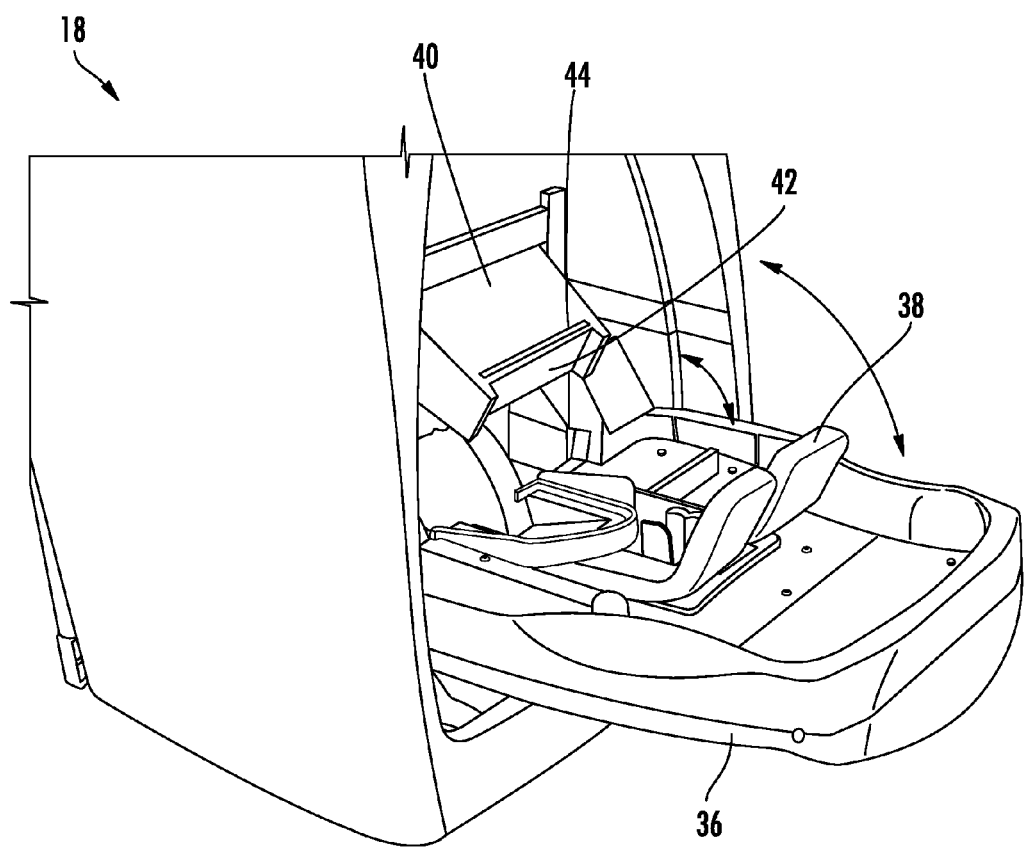
FIG. 4 is a perspective view of the preferred embodiment of the emergency eyewash station of the present invention with the actuator arm assembly deployed to the open position and the headrest pulled forward.
Figure 9:
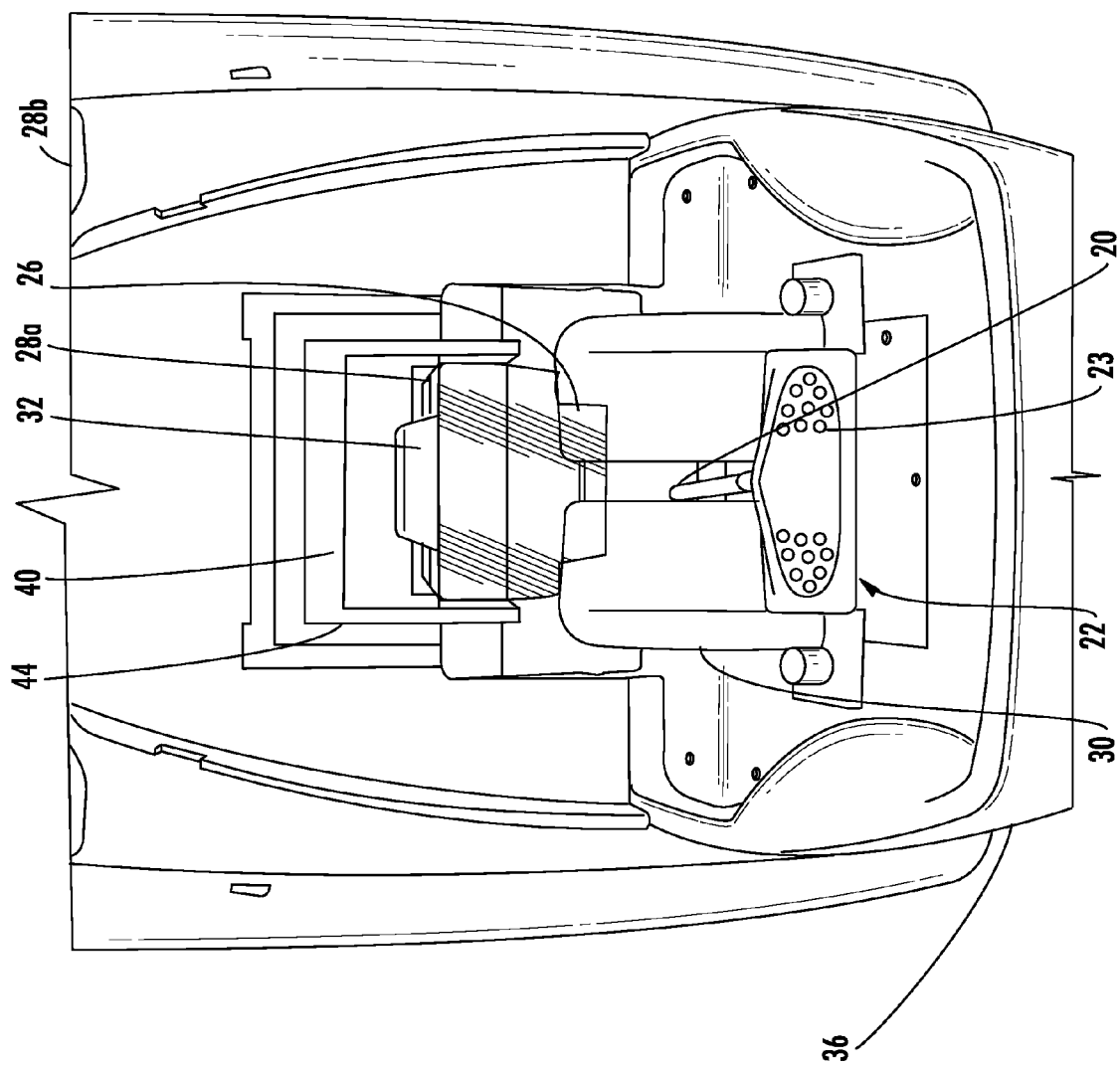
FIG. 9 is a front perspective view of the emergency eyewash station of the present invention with the actuator arm assembly in the fully open position.

Referring to FIG. 4, the main body of the eyewash station 10 includes a pivoting actuator arm assembly 36. The actuator arm assembly 36 can be pivoted from an upright closed position (as seen in FIG. 1) to an activated or open prone position (as seen in FIGS. 4 and 9). When in the closed position, the actuator arm assembly 36 conforms to the main body portion to present a uniform appearance and prevent accidental discharge of the eyewash station 10. Although it is preferred that the actuator arm assembly 36 pivot downwardly, one-skilled in the art would appreciate that the actuator arm assembly 36 could be configured and arranged to slide or pivot in another direction as desired with equally effective results.

The actuator arm assembly 36 also includes a headrest 38 to help the user of the eyewash station 10 properly align his or her eyes with the eyepiece 23 of the dispensing structure 22. As shown in FIG. 4, the headrest 38 conveniently folds forward and out of the way to allow the eyewash station 10 of the present invention to be easily armed and inspected. In particular, the user may fold the headrest 38 out of the way to be able obtain access to the interior of the device through an access port to be able to feed the dispensing hose 20 therethrough. During use, the headrest 38 is folded rearward, as shown in FIG. 9. The headrest 38 also has a central channel for the hose 20 to nestle in during and prior to actuation of the emergency eyewash station 10.

Figure 5:
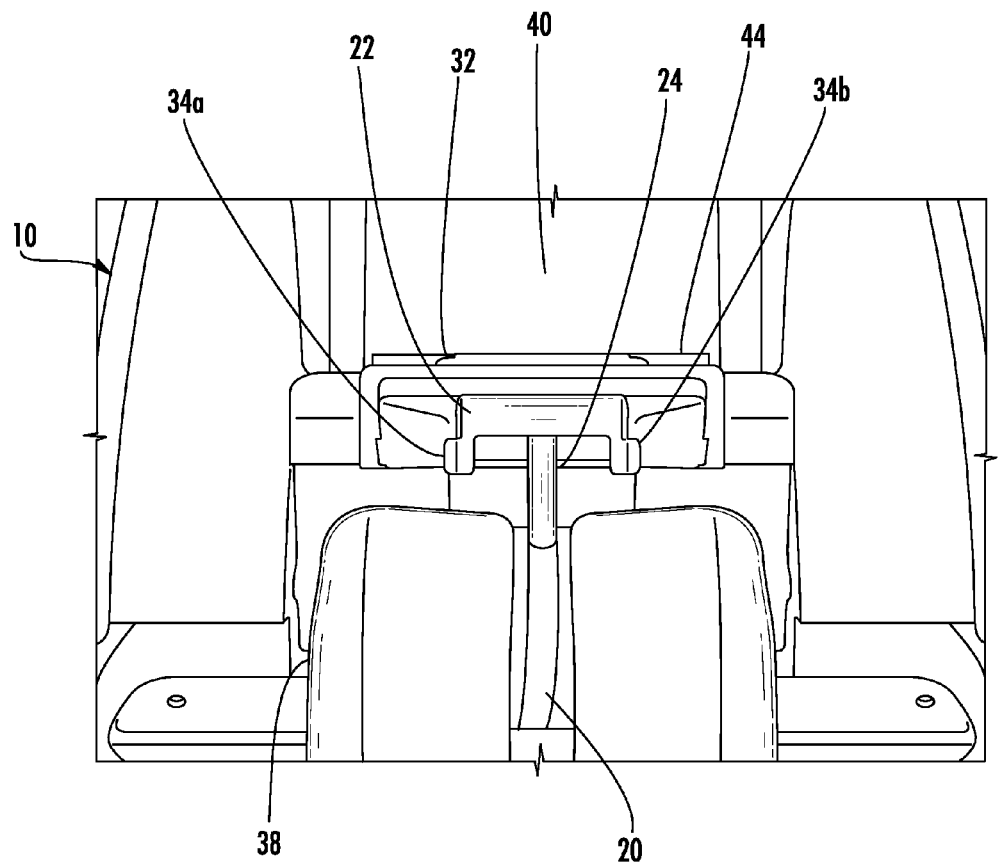
FIG. 5 is a front perspective view of the dispensing structure connected to the projection of the emergency eyewash station of the present invention.
Figure 6:
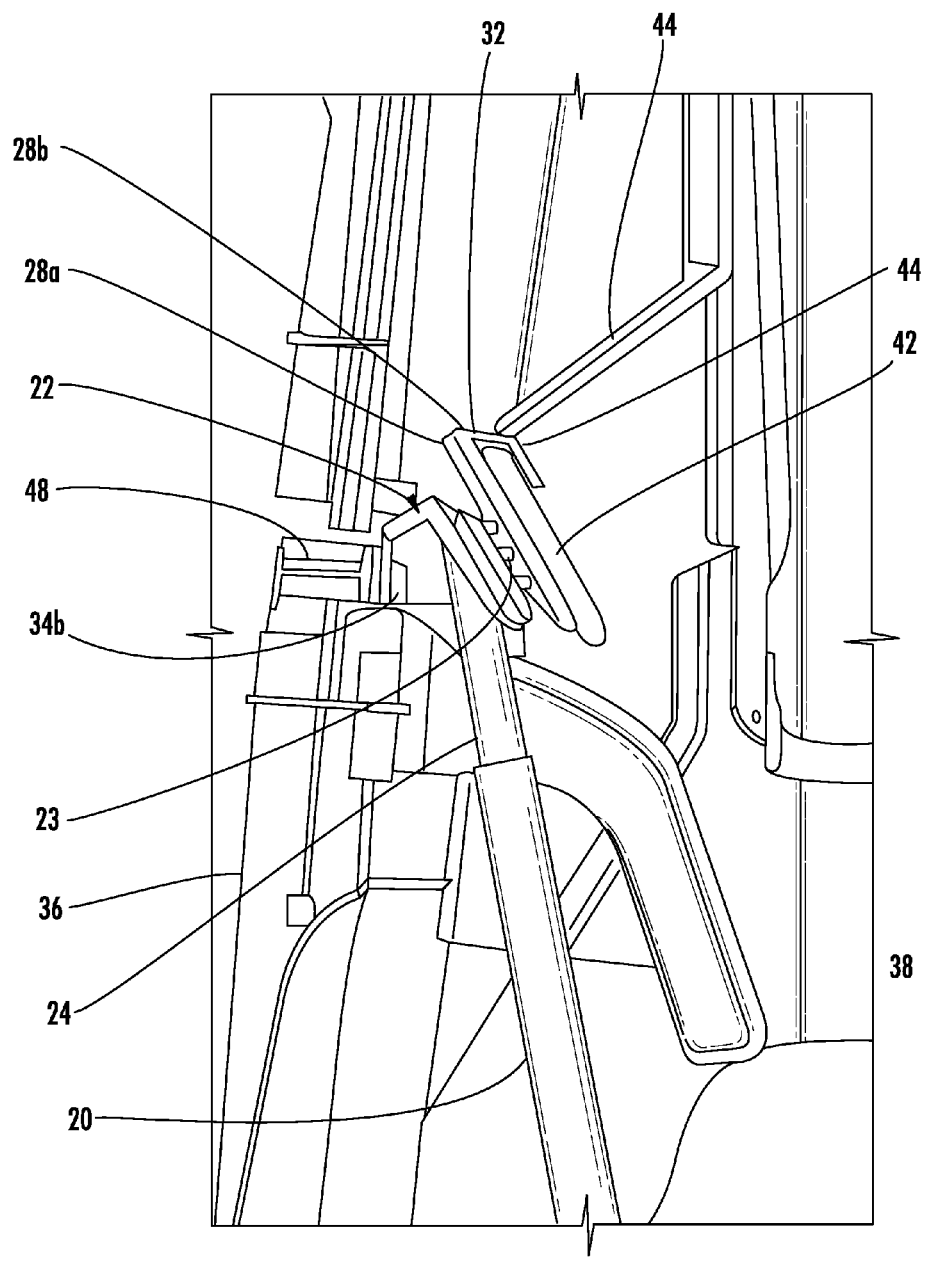
FIG. 6 is a side cross-section through line 6-6 of FIG. 1.

Referring now to FIGS. 4-6, within the main dispensing unit and behind the actuator arm assembly 36 (while in the upright closed position) there is a projection 40 with a front face 42 and a slot 44 on a top edge of the projection 40. To arm the eyewash station 10, the dispensing structure 22 is connected to the projection 40 by sliding the spring arm 32 of the clip body 28a, 28b into the slot 44, as shown in FIGS. 5-6. The clip body 28a, 28b is held against the front face 42 of the projection 40 by the spring arm 32.

Figure 7:
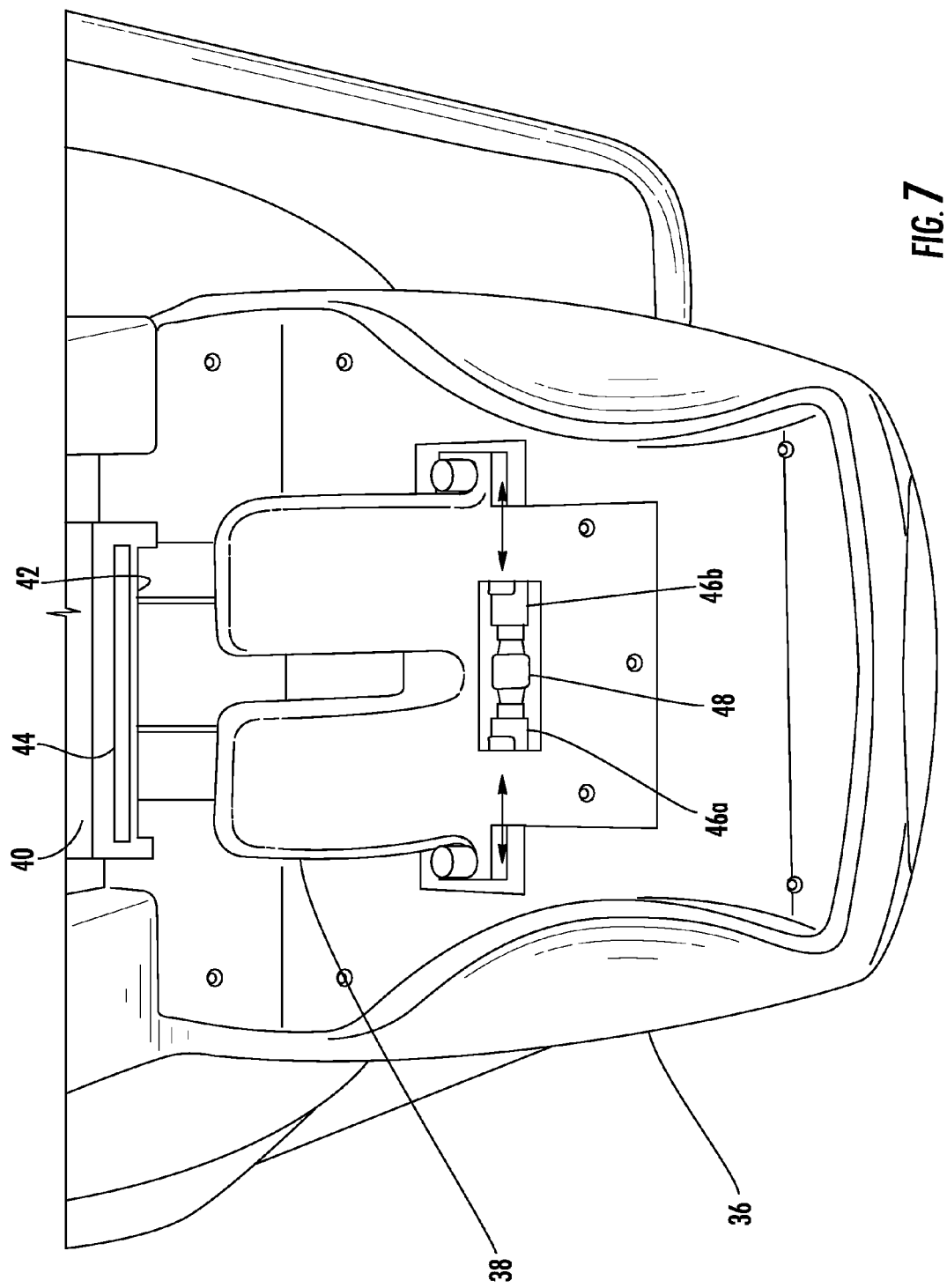
FIG. 7 is a top perspective view of the actuator arm assembly of the emergency eyewash station of the present invention.

Referring now to FIG. 7, on the actuator arm assembly 36 is a pair of inwardly spring-biased locking members 46a, 46b. The spring-biased locking members 46a, 46b may be forced apart by depressing a release button 48 on the front of the actuator arm assembly 36, best viewed in FIG. 1. Referring back to FIG. 7 now, the release button 48 has a wedged-shaped projection that forces the locking members 46a, 46b apart when the release button 48 is depressed. The release button 48 allows for convenient inspection of the eyewash station 10, without discharging the station accidentally.

When the actuator arm assembly 36 is pivoted to the upright and closed position, the locking members 46a, 46b couple to the hooks 34a, 34b on the dispensing structure 22. In particular, the sloped surfaces of the hooks 34a, 34b force the locking members 46a, 46b apart and to allow the locking members 34a, 34b to pass over and couple to the hooks 46a, 46b. With the spring arm 32 secured to the projection 40 and the locking members 46a, 46b secured to the hooks 34a, 34b on the dispensing structure 22, the emergency eyewash station 10 is now armed and ready for use.

Figure 8:
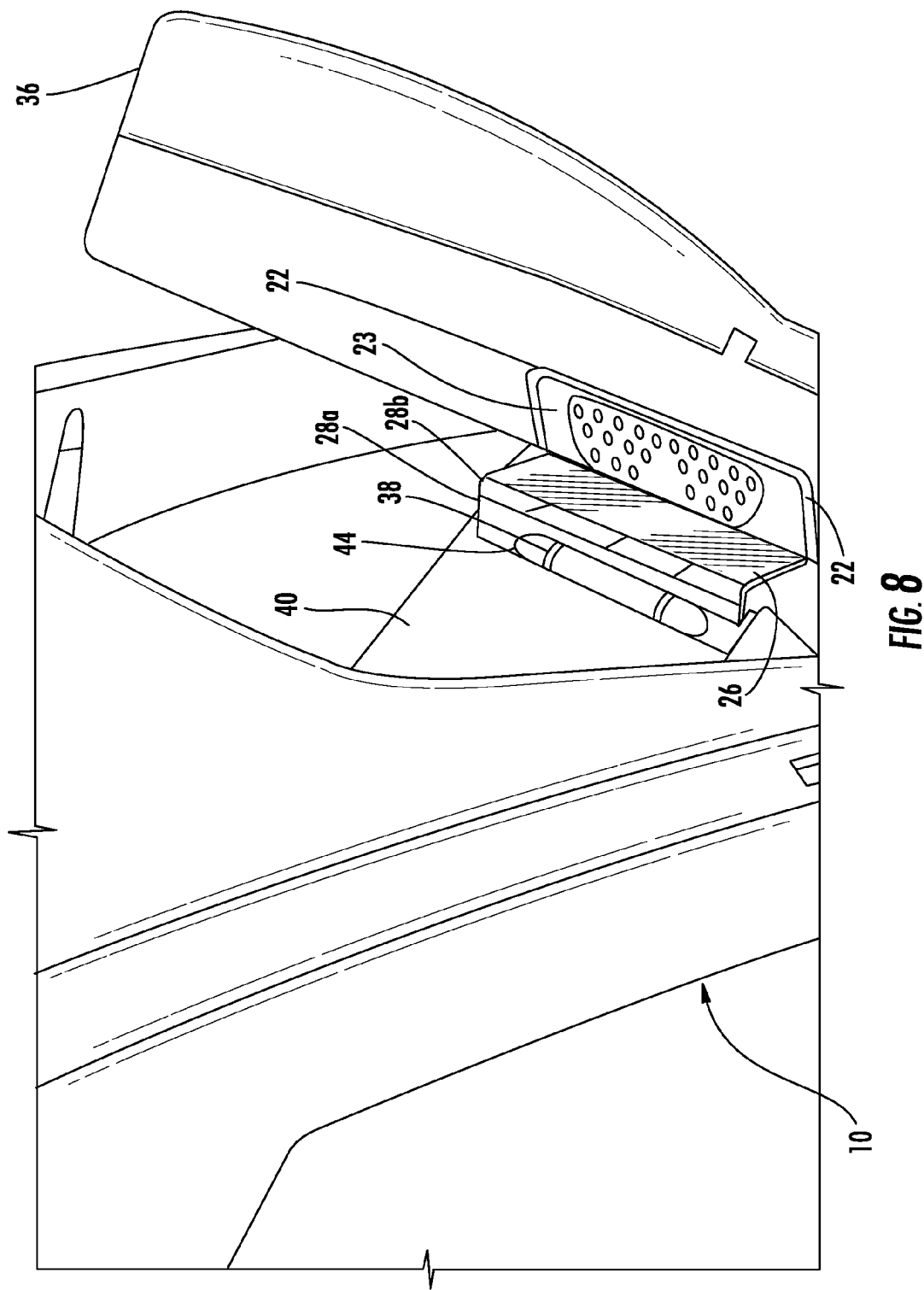
FIG. 8 is a top perspective view of the emergency eyewash station of the present invention with the actuator arm assembly being activated, which illustrates the membrane being peeled free from the eyepiece of the dispensing structure.

Referring to FIGS. 8-9, pulling on the actuator arm assembly 36 causes the dispensing structure 22 to separate from the clip body 28a, 28b, thereby freeing the membrane 26 from the eyepiece 23. Specifically, as shown in FIG. 8, as the actuator arm assembly 36 pivots, the clip body 28a, 38b remains secured to the projection 40 by the spring arm 32. Because the tab 27 of the membrane 26 is securely held within the to portions of the clip body 28a, 28b and the dispensing structure 22 is securely held in the actuator arm assembly 36 by the locking members 46a, 46b, the membrane 26 is peeled away from the eyepiece 23 of the dispensing structure 22 as the actuator arm assembly 36 pivots downwardly to the open position. As seen in FIG. 9, once the actuator arm assembly 36 is pivoted to the open position, the membrane 26 has been completely separated from the eyepiece 23 of the dispensing structure 22 and the eyewash fluid may dispense freely therefrom.

Therefore, it can be seen that the present invention provides a unique solution to the problems of the prior art by providing an emergency eyewash station that uniquely providing an emergency eyewash station including an improved cartridge assembly having a sterile "bag" or bladder with a fluid hose having a sealed eyepiece on a dispensing structure at one end, and an actuation mechanism to tear the seal free from the eyepiece upon actuation of the unit.

It would be appreciated by those skilled in the art that various changes and modifications can be made to the illustrated embodiments without departing from the spirit of the present invention. All such modifications and changes are intended to be within the scope of the present invention except as limited by the appended claims.

What is claimed is:

1. An emergency eyewash station, comprising:
   a main body configured and arranged to hold and dispense eyewash fluid therefrom;
   an actuator arm assembly movable from a closed position to an open position;
   a dispensing structure having an eyepiece with a membrane sealing said eyepiece closed,
   said eyepiece in fluid connection with the eyewash fluid contained in the main body; and
   said dispensing structure removably coupled to said actuator arm assembly whereby when said actuator arm assembly is moved from the closed position to the open position said membrane is unsealed and the eyewash fluid dispenses from said eyepiece
   wherein said dispensing structure further comprises: a tab extending from said membrane.

2. The device of claim 1, wherein said dispensing structure further comprises:
   a clip body configured and arranged to clasp said tab and removably couple to said eyepiece.

3. The device of claim 2, wherein said clip body further comprises a spring arm configured and arranged to couple to said main body.

4. The device of claim 3, further comprising:
   a projection having an opening defining a slot configured to slidably receive said spring arm thereon.

5. The device of claim 1, further comprising:
   a pair of opposing hooks extending from a rear face of said dispensing structure;
   said pair of opposing hooks configured and arranged to cooperate with a pair of spring-biased locking members in said actuator arm assembly to removably couple said dispensing structure thereto.

6. The device of claim 1, further comprising a release button to selectively decouple said dispensing structure from said actuator arm assembly.

7. The device of claim 1, where said actuator arm assembly is configured and arranged to pivot from said closed position to said open position.

8. The device of claim 1, further comprising a removable cartridge assembly hung within said main body for containing the eyewash fluid.

9. The device of claim 1, further comprising a headrest extending from said actuator arm assembly.

10. A dispensing structure for an emergency eyewash station, comprising:
    an eyepiece configured and arranged to dispense eyewash fluid therethrough; and
    a membrane sealing said eyepiece closed;
    further comprising: a tab extending from said membrane.

11. The article of claim 10, further comprising:
    a clip body configured and arranged to clasp said tab and removably couple to said eyepiece.

12. The article of claim 11, wherein said clip body further comprises:
    a first portion;
    a second portion hingedly connected to said first portion and foldable to a closed position wherein the first portion couples to said second portion and keeps the first portion and said second portion folded in the closed position;
    said tab being sandwiched between said first portion and said second portion and securely held therewithin.

13. The article of claim 11, wherein said clip body further comprises a spring arm configured and arranged to couple to a first portion of said emergency eyewash station.

14. The article of claim 10, further comprising:
    a pair of opposing hooks extending from a rear face of said dispensing structure;
    said pair of opposing hooks configured and arranged to be removably coupled to a portion of said emergency eyewash station.

* * * * *